(12) United States Patent
Oommen et al.

(10) Patent No.: US 9,957,500 B2
(45) Date of Patent: May 1, 2018

(54) CONTINUOUS FLOW NUCLEIC ACID EXTRACTION APPARATUS AND METHOD OF USE THEREOF

(71) Applicant: STEM ARTS PROJECTS, LLC, Lincoln, NE (US)

(72) Inventors: Abraham Oommen, Lincoln, NE (US); Matthew Greenleaf, Lincoln, NE (US); Adam Koch, Lincoln, NE (US)

(73) Assignee: Stem Arts Projects, LLC, Lincoln, NE (US)

(*) Notice: Subject to any disclaimer, the term of this patent is extended or adjusted under 35 U.S.C. 154(b) by 396 days.

(21) Appl. No.: 14/632,919

(22) Filed: Feb. 26, 2015

(65) Prior Publication Data
US 2016/0251647 A1 Sep. 1, 2016

(51) Int. Cl.
| B01D 35/00 | (2006.01) |
| B01D 41/00 | (2006.01) |
| C12N 15/10 | (2006.01) |
| C12Q 1/68  | (2018.01) |

(52) U.S. Cl.
CPC ......... *C12N 15/101* (2013.01); *C12Q 1/6806* (2013.01)

(58) Field of Classification Search
None
See application file for complete search history.

(56) References Cited

U.S. PATENT DOCUMENTS

| 5,380,492 A * | 1/1995 | Seymour | A61B 10/0051 422/401 |
| 5,876,372 A * | 3/1999 | Grabenkort | A61M 5/31596 604/89 |
| 6,234,196 B1 * | 5/2001 | Fischer | B01F 5/0685 137/493.8 |
| 8,454,558 B2 | 6/2013 | Jessop | |
| 2001/0037091 A1 * | 11/2001 | Wironen | A61B 17/8816 604/236 |
| 2003/0215845 A1 | 11/2003 | Bille | |
| 2004/0110167 A1 * | 6/2004 | Gerdes | C12Q 1/6834 435/6.11 |
| 2004/0122359 A1 * | 6/2004 | Wenz | A61M 5/31511 604/82 |
| 2005/0177100 A1 * | 8/2005 | Harper | A61M 5/31596 604/89 |
| 2005/0197538 A1 * | 9/2005 | Leaton | A61B 90/70 600/218 |
| 2009/0112157 A1 * | 4/2009 | Jessop | A61C 9/0026 604/91 |
| 2010/0323322 A1 * | 12/2010 | Jessop | B65D 25/082 433/90 |
| 2013/0330250 A1 * | 12/2013 | Koeda | C12N 15/1013 422/527 |
| 2016/0348092 A1 | 12/2016 | Stray et al. | |

OTHER PUBLICATIONS

Ex parte James Stray, Jason Yingjie Liu, Maxim Brevnov, Jaiprakash Shewale, and Allison Holt, decision of the Patent Trial and Appeal Board, Appeal No. 2014-001388, U.S. Appl. No. 12/882,194 , 7 pages.

* cited by examiner

*Primary Examiner* — Jill A Warden
*Assistant Examiner* — Brittany I Fisher
(74) *Attorney, Agent, or Firm* — AriAnna C. Goldstein; Baird Holm LLP

(57) ABSTRACT

A continuous flow nucleic acid extraction apparatus comprising a piston column apparatus for the extraction of nucleic acids from a nucleic acid sample. The disclosure also includes a method of using the continuous flow nucleic acid extraction apparatus.

9 Claims, 3 Drawing Sheets

CONTINUOUS FLOW NUCLEIC ACID EXTRACTION APPARATUS AND METHOD OF USE THEREOF

BACKGROUND

Nucleic acid extraction from biological samples is carried out by a variety of apparatuses and methods for the subsequent testing of nucleic acids. Such apparatuses and methods are necessary in the subsequent diagnostic testing of nucleic acids.

SUMMARY

Accordingly, an embodiment of the present disclosure includes an apparatus and method of use for a continuous flow nucleic acid extraction apparatus. The present disclosure provides a unique apparatus for extraction of nucleic acids in a single column. Constraining the nucleic acid extraction to a single column provides advantages.

It is to be understood that both the foregoing general description and the following detailed description are exemplary and explanatory only and are not necessarily restrictive of the disclosure as claimed. The accompanying drawings, which are incorporated in and constitute a part of the specification, illustrate embodiments of the disclosure and together with the general description, serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the embodiments of the present disclosure, examples of which are illustrated in the accompanying drawings. Described herein is a continuous flow nucleic acid extraction apparatus. Also described herein is the method of use of the continuous flow nucleic acid extraction apparatus.

Figure 1:
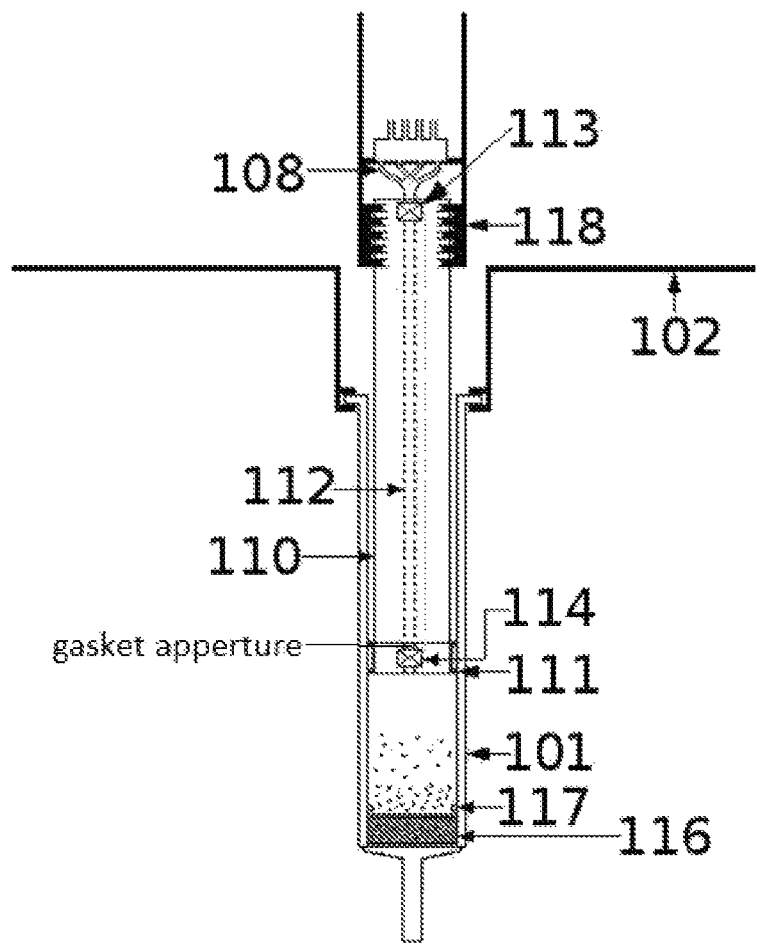
FIG. 1 is a cross sectional view of a piston column apparatus in accordance with an exemplary embodiment of the present disclosure.

Referring to FIG. 1, the present disclosure shows the piston column apparatus 100 portion of the continuous flow nucleic acid extraction apparatus 200. The piston column apparatus 100 described herein comprises a piston 110 with an aperture 112 extending from the proximal end to the distal end of the piston 110. In embodiments the piston 110 fits within a column 101 having a matrix 116 disposed therein. The aperture 112 may be of any shape, but in the present embodiment is a cylindrical aperture. A first valve 113 and a second valve 114 are attached to the piston 110 and are positioned over the proximal end of the aperture 112 and the distal end of the aperture 112 respectively. In embodiments, the first valve 113 and second valve 114 may be valves configured for being opened and closed manually by a user. In further embodiments, the first valve 113 and second valve 114 may be configured for being opened and closed automatically with a valve actuator for example. Also attached to the distal end of the piston 110 is a gasket 111 having a gasket aperture. In embodiments the gasket aperture is of similar size to the aperture 112 on the piston 110. For example, the gasket is a rubber gasket that fits tightly onto the distal end of the piston 110 such that the gasket aperture of the gasket 111 lines up with the aperture 112 of the piston 110. Attached to the proximal end of the piston 110 is a clasping arm 118. In embodiments the clasping arm 118 may be permanently affixed to the piston 110. In further embodiments the clasping arm 118 may open and close for removal of the piston 110. Attached to the first valve 113 is a buffer conduit 108. In embodiments the buffer conduit is plastic tubing that fits into the first valve 113 that allows fluid to pass through the buffer conduit 108 and first valve 113 and into the aperture 112 of the piston 110.

Referring to FIG. 1., contacting the distal end of the piston 110 is the column 101. In embodiments the column 101 is a cylindrical tube of a diameter slightly larger than the piston 110. For example, the piston 110 fits tightly within the column 101. In embodiments the column 101 has a proximal end and a distal end, where the matrix 116 is located at the distal end of the column 101. In embodiments the matrix 116 may be a material in powder or membrane form that has the capability to bind nucleic acids (e.g. a nucleic acid matrix). In further embodiments, a matrix could also be defined as a material in powder or membrane form that has the capability to bind cellular components (e.g. protein, carbohydrates, and cell debris), except nucleic acids (e.g. a cellular component matrix). In further embodiments, the column 101, at a location distal to the matrix 116, is tapered into a funnel shape configured for allowing fluid to exit the column 101. In further embodiments, the column 101, at a location proximal to the matrix 116 may have a stopping point 117 at which the piston 110 stops. In embodiments the column may be used for a single nucleic acid extraction (e.g. disposable column).

Figure 2:
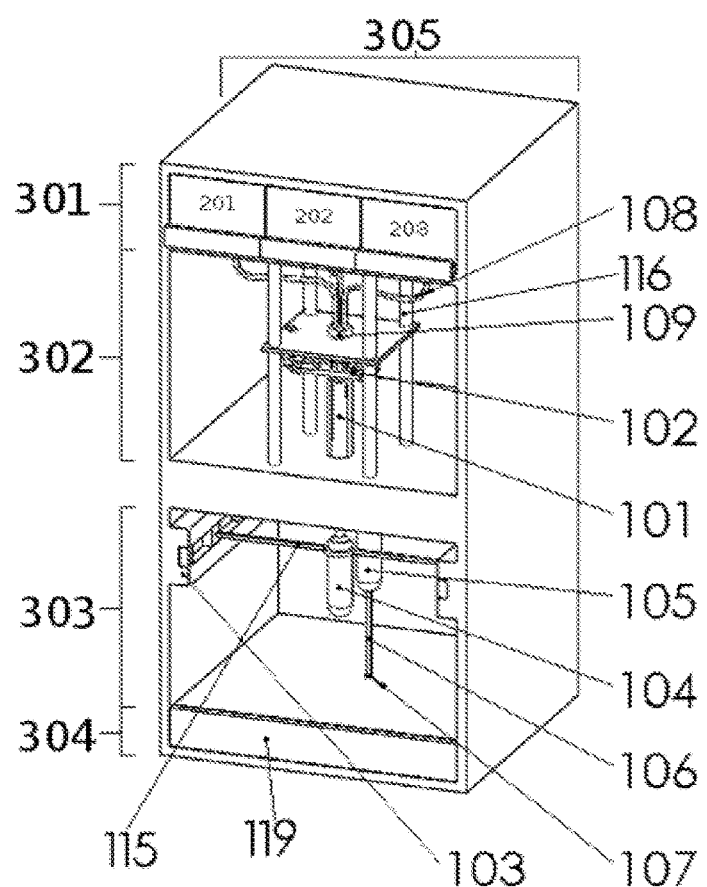
FIG. 2 is a continuous flow apparatus in accordance with an exemplary embodiment of the present disclosure.

Referring to FIG. 2, the present disclosure shows a continuous flow nucleic acid extraction apparatus 200. The continuous flow nucleic acid extraction apparatus 200 comprises a structural assembly 305 having a buffer reservoir assembly portion 301, a column mounting assembly portion 302, a rail assembly portion 303, and a waste assembly portion 304. In embodiments, the buffer reservoir assembly portion 301 contains one or more buffer tanks 201, 202, 203, connected to the buffer reservoir assembly portion. In embodiments the buffer reservoir assembly portion may contain a plurality of buffer tanks. In further embodiments the buffer tanks 201, 202, 203 are operationally coupled with the buffer conduit 108. For example, the buffer tanks 201, 202, and 203 may be rectangular in shape and configured for holding a fluid, such as a buffer, and delivering the buffer to the buffer conduit 108. For example, on the proximal side of each buffer tank there will be a resealable cap for the introduction of buffer into the buffer tanks, and on the distal side of each buffer tank there will be an opening wherein the proximal end of the buffer conduit 108 is operationally coupled to the buffer tank. A pump 109 is attached to the buffer tanks and the buffer conduit 108, the pump 109 configured for controlling the flow of buffer from each buffer tank. In embodiments the pump 109 may be a peristaltic pump. In embodiments with more than one buffer tank, the peristaltic pump 109 may be a multi-channeled peristaltic pump. For example, a user may cause delivery of the buffer to the aperture 112 by turning the channel of peristaltic pump 109 operationally coupled with one of the buffer tanks, such as buffer tank 201, to the on position allowing the buffer to move into the buffer conduit 108.

Referring to FIG. 1, the buffer conduit 108 is attached to the first valve 113. In embodiments the first valve may be a multi-channel valve configured for attachment of one or more buffer conduits 108 for delivery of the buffer to the aperture 112 of the piston 110.

Referring to FIG. 2, the piston column apparatus 100 portion is attached to the structural assembly 305 at the column mounting assembly portion 302. In embodiments, the column mounting assembly portion 302 may include one or more vertical pillars 116 attached to the distal side of the buffer reservoir assembly portion 301 and extending downward where they are attached at the distal side of the column mounting assembly portion 302. For example, the column mounting assembly portion 302 may include four vertical pillars. A platform 102 may be attached to the vertical pillars 116, such that the platform 102 is suspended between the vertical pillars 116. In embodiments the platform 102 may have an aperture configured for receiving the piston column apparatus. Referring to FIG. 1 for example, the piston 110 may be proximal to the platform 102 and the column 101 may be distal to the platform 102. The column 101 is attached to the platform 102 via a tongue and groove locking mechanism wherein the groove portion surrounds the aperture of the platform 102 and where the corresponding tongue portion resides on the proximal end of the column 101.

Referring to FIG. 2, a waste collection tube 105 contacts the distal end of the column 101 via the rail assembly portion 303 of the structural assembly 305. In embodiments the waste collection tube 105 is attached to a rail 103. In embodiments the waste collection tube 105 is a cylindrical collection tube with an aperture in the distal end of the waste collection tube 105 where a waste conduit 106 is attached. In embodiments the rail 103 comprises a chain 115 and pulley system wherein there are two pulleys generally opposite each other with the chain 115 running through each pulley such that the chain 115 forms an oblong shape. For example, the waste collection tube 105 is attached to the chain 115 of the rail 103 on one side of the oblong shape via a holder. In embodiments the rail 103 is attached horizontally to the rail assembly portion 303 via a tongue and groove mechanism. For example, opposite vertical walls of the rail assembly 303 have a groove portion, and the rail 103 acts as the tongue portion by sliding into the groove. For example, the pulleys of the rail 103 reside in each respective groove of the rail assembly portion 303. In embodiments, the chain may move horizontally via the pulleys. In further embodiments, the rail 103 may move front to back on a traverse plain by sliding the rail 103 along the groove of the rail assembly portion 303. In further embodiments, the rail 103 may move horizontally and transverse via a stepper motor operationally coupled to the groove of the rail assembly portion 303 and the pulley of the rail 103.

Referring to FIG. 2, a sample collection tube 104 is attached to the chain 115 of the rail 103. In embodiments, the sample collection tube 104 is attached to the chain 115 via a holder. For example, the sample collection tube 104 is on the opposite side of the chain 115 separated by the pulleys, such that the sample collection tube 104 is generally opposite the waste collection tube 105. In embodiments the sample collection tube 104 is a cylindrical collection tube. In further embodiments, one or more sample collection tubes may be attached to the chain 115.

Referring to FIG. 2 the waste conduit 106 is attached to the distal side of the column 101 and the opposite end of the waste conduit 106 is attached to a waste collection port 107. In embodiments the waste conduit 106 is plastic tubing, and the port 107 is a one-way port that allows for the movement of fluid through the port only in one direction. In embodiments, the waste port 107 is attached to the proximal side of a waste collection tank 119. The waste collection tank 119 is attached to the waste assembly portion 304 of the structural assembly 305. In embodiments, the waste collection tank is a rectangular tank configured for holding a fluid, such as a waste buffer, with a port on the distal side of the waste collection tank 119 configured for allowing waste buffer to exit the waste collection tank 119 and exit the continuous flow nucleic acid extraction apparatus 200.

Figure 3:
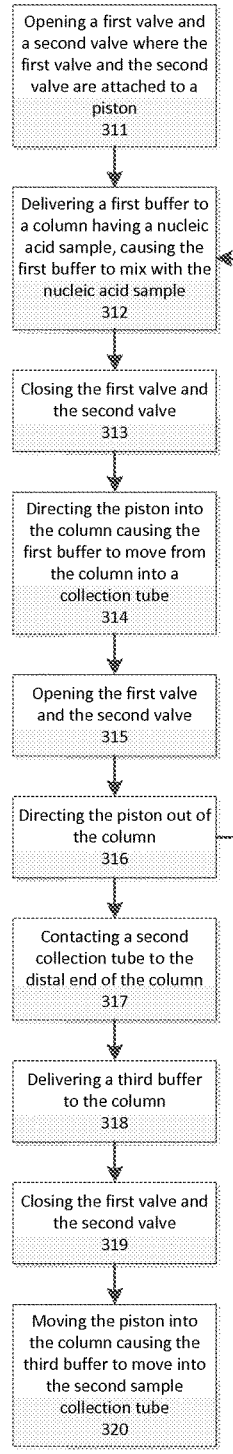
FIG. 3 is a flow chart illustrating a method for extraction of a nucleic acid sample using the continuous flow apparatus.

Referring to FIG. 3 described herein is a method for using the continuous flow nucleic acid extraction apparatus 200 to extract nucleic acid from a nucleic acid sample. In some embodiments the nucleic acid sample to be analyzed may be blood, muscle tissue, plasma, semen, cells, cheek swabs, nasal swabs, hair follicles and any other tissue or buffer wash from a biological specimen as well as preserved biological samples including frozen samples. The nucleic acid sample of a volume, for example of one hundred (100) micro liters (µl), is placed in the column 101, and the column 101 is fit into the platform 102 of the column mounting assembly portion 302.

In embodiments, the method 300, includes a step of opening the first valve 113 and the second valve 114 (Step 311). The first valve 113 and the second valve 114 may be opened manually by a user, or the first valve 113 and the second valve 114 may be opened automatically, for example, with an electronic valve actuator.

In embodiments, the method 300, includes a step of delivering a first buffer to the column 101 via the buffer conduit 108 (Step 312). In some embodiments a pump 109 delivers the buffer to the column 101. For example, a peristaltic pump may be used to deliver the buffer to the column 101. In embodiments, the matrix 116 may be a nucleic acid matrix, such that the nucleic acid sample being analyzed may require cell lysing/hybridization, washing, and elution steps. For example, the nucleic acid sample may be a mammalian whole blood sample requiring a buffer for cell lysis and hybridization, such as chaotropic salts (e.g. guanidine hydrochloride) in high concentrations (e.g. 6.5 molar (M)), a buffer for washing, such as alcohol (e.g. isopropanol or ethanol) and water at a 70:30 or 80:20 ratio or Tris-Ethylenediaminetetraacetic acid (Tris-EDTA), and a buffer for elution of the nucleic acid sample from the matrix, such as a low salt or no salt buffer (e.g. 0.1×Tris-EDTA). In further embodiments the matrix 116 may be a cellular component matrix, such that the nucleic acid sample only requires cell lysing and hybridization of other cellular components. For example, the nucleic acid sample may be a mammalian whole blood sample requiring a buffer for cell lysis and hybridization of other cellular components, such as a 10 millimolar (mM) Tris-hydrochloride (HCl) (pH 8.0), 100 mM sodium chloride (NaCl), 10 mM EDTA, 0.5% sodium dodecyl sulfate (SDS) and 1 microgram/microliter (µg/µl) final concentration of Proteinase K. In embodiments delivering the first buffer to the column includes delivering a volume of the cell lysis/hybridization buffer equal to five times the volume of the nucleic acid sample (e.g. 500 µl). For example, where the matrix 116 is a nucleic acid matrix the first buffer is a chaotropic salt (e.g. guanidine hydrochloride) in high concentrations (e.g. 6.5 M), or for example, where the matrix 116 is a cellular component matrix the first buffer is 10 mM Tris-HCl (pH 8.0), 100 mM NaCl, 10 mM EDTA, 0.5% SDS and 1 µg/µl final concentration of Proteinase K. In embodiments, after delivering the first buffer a specified amount of time may pass, such as two to five minutes, to allow for cell lysis and hybridization.

In embodiments, the method 300, includes a step of closing the first valve 113 and the second valve 114 (Step 313). In embodiments, the first valve 113 and the second valve 114 may be closed manually. In further embodiments the first valve and the second valve may be closed automatically, for example, with an electronic valve actuator. Closing the first valve 113 and the second valve 114 seals the system, such that pressure may be created within the column 101 to move the buffer through the matrix 116 and out of the column 101.

In embodiments, the method 300 includes a step of directing the piston 110 into the column 101 (Step 314). In embodiments the gasket 111 creates a seal with the column 101, which in conjunction with the closed first valve 113 and closed second valve 114, causes the air pressure inside the column 101 to increase when the piston 110 is directed into the column 101, forcing the buffer through the matrix 116 and out of the column 101 into a first collection tube. In embodiments the movement of the piston 110 is completed via a stepper electric motor. In embodiments, the piston 110 moves into the column 101 to a stopping point 117 that is proximal to the matrix 116. In embodiments, where the matrix 116 is a nucleic acid matrix the first collection tube is a waste collection tube 105, wherein the first buffer moves from the waste collection tube 105, into the waste conduit 106, through the waste port 107, and into the waste collection tank 119. In further embodiments, where the matrix 116 is a cellular component matrix the first collection tube may be a sample collection tube 104, wherein the first buffer, including the extracted nucleic acids, moves into the sample collection tube 104.

In embodiments, the method 300 includes a step of opening the first valve 113 and the second valve 114 (Step 315). Opening the first valve 113 and the second valve 114 allows the air pressure inside the column 101 to equalize. In embodiments the first valve 113 and the second valve 114 may be opened manually. In further embodiments the first valve 113 and the second valve 114 may be opened automatically, for example, with an electronic valve actuator.

In embodiments, the method 300 includes a step of directing the piston 110 out of the column 101 (Step 316). Because the air pressure inside the column 101 is equalized in step 315, the piston 110 may be directed out of the column 101 without creating a negative pressure or a vacuum inside the column 101, which avoids causing the buffer or nucleic acid sample to be drawn back up through the matrix 116 or the matrix itself to be drawn back up through the column 101. In embodiments the piston 110 may be directed out of the column 101 by a stepper electric motor. In embodiments the stepper electric motor may be controlled manually or automatically.

In embodiments, the method 300 includes repeating steps 312, 313, 314, 315, and 316 with a washing buffer. In embodiments where the matrix 116 is a nucleic acid matrix, the washing buffer may be a buffer configured for washing the nucleic acid sample, such as alcohol (e.g. isopropanol or ethanol) and water or 1×Tris-EDTA at a 70:30 or 80:20 ratio. For example, in step 312, delivering the washing buffer to the nucleic acid sample may include delivering a volume of twelve times the nucleic acid sample volume (e.g. 1200 μl) to the column and waiting for a period of time (e.g. 15 to 20 minutes) before proceeding to step 313 In further embodiments, Step 312 may include delivering the washing buffer to the nucleic acid sample in a volume of six times the nucleic acid sample (e.g. e.g. 600 μl), waiting for a period of time (e.g. 15 to 20 minutes) before proceeding to step 313. In embodiments, the method 300 may include repeating Steps 312, 313, 314, 315, and 316 with a plurality of washing buffers. In embodiments where the matrix 116 is a nucleic acid matrix, the washing buffer may be configured for washing the nucleic acid sample. For example, Steps 312, 313, 314, 315, and 316 may be repeated with a second and a third washing buffer where the second washing buffer is alcohol (e.g. isopropanol or ethanol) and water or 1×Tris-EDTA at a 70:30 or 80:20 ratio, and the third washing buffer is alcohol (e.g. isopropanol or ethanol) and water or 1×Tris-EDTA at a 70:30 or 80:20 ratio. Step 312 may include delivering the second washing buffer and the third washing buffer to the nucleic acid sample in a volume of twelve times the nucleic acid sample volume (e.g. 1200 μl) and waiting for a period of time (e.g. 15 to 20 minutes) before proceeding to step 313. In further embodiments, Step 312 may include delivering the second and third washing buffer to the nucleic acid sample in a volume of six times the nucleic acid sample (e.g. e.g. 600 μl), waiting for a period of time (e.g. 15 to 20 minutes) before proceeding to step 313.

In embodiments, the method 300 includes the step of contacting a second collection tube with the distal end of the column 101 (Step 317). In embodiments where the matrix 116 is a nucleic acid matrix the second collection tube is a sample collection tube 104, wherein the sample collection tube 104 contacts the column 101 via movement of the rail 103. For example, the rail 103 moves backward on the traverse plane such that the sample collection tube 104 moves to contact the column 101, while the waste collection tube 105 moves away from the column 101. In embodiments with more than one sample collection tube the chain 115 of the rail 103 may also move horizontally wherein a sample collection tube will contact the column 101. In further embodiments where the matrix 116 is a cellular component matrix, the second collection tube is a waste collection tube 105, wherein the waste collection tube 105 contacts the column 101 via movement of the rail 103. For example, the rail 103 moves forward on the traverse plane such that the waste collection tube 105 moves to contact the column 101, while the sample collection tube 104 moves away from the column 101. In embodiments the rail moves forward and/or backward in the traverse plan and the chain 115 moves horizontally via a stepper motor attached to the rail 103.

In embodiments, the method 300 includes a step of delivering a third buffer to the column 101 (Step 318). In embodiments where the matrix 116 is a nucleic acid matrix, the third buffer is configured for eluting the nucleic acid sample from the matrix 116. In embodiments where the matrix 116 is a cellular component matrix, the third buffer is configured for eluting cellular components from the matrix 116. In embodiments, delivering the third buffer to the column 101 may include a volume of the third buffer equal to the volume of the nucleic acid sample (e.g. 100 μl). In embodiments after delivering the third buffer a specified amount of time may pass (e.g. 3 to 5 minutes), to allow for elution.

In embodiments, the method 300 may include a step of closing the first valve 113 and the second valve 114 (Step 319). Closing the first valve 113 and the second valve 114 seals the system, such that pressure may be created within the column 101 to move the third buffer through the matrix and out of the column 101. In some embodiments the closing of the first valve 113 and the second valve 114 may be manual. In further embodiments the closing of the first valve 113 and the second valve 114 may be automatic, for example, by an electronic valve actuator.

In embodiments, the method 300 may include a step of directing the piston 110 into the column 101 (Step 320). The gasket 111 creates a seal with the column 101, which in conjunction with the closed first valve 113 and closed second valve 114, increase the air pressure inside the column 101 when the piston 110 moves into the column 101, forcing the third buffer through the matrix 116 and out of the column 101 into the second sample collection tube. In embodiments the movement of the piston 110 is completed via a stepper electric motor. In embodiments, the piston 110 moves into the column 101 to the stopping point 117 that is proximal to the matrix 116. In embodiments where the matrix 116 is a nucleic acid matrix, the third buffer will also include the nucleic acid sample, wherein the sample collection tube 104 may be removed from the rail assembly 303 for further diagnostic testing. In further embodiments where the matrix 116 is a cellular component matrix, the third buffer moves from the waste collection tube 105, into the waste conduit 106, through the waste collection port 107, and into the waste collection tank 119. The sample collection tube 104 wherein the nucleic acid was previously eluted in steps 312, 313, 314, 316 may be removed from the rail assembly 303 and used for further diagnostic testing.

It is to be noted that the foregoing described embodiments may be conveniently implemented using conventional general purpose digital computers programmed according to the teachings of the present specification, as will be apparent to those skilled in the computer art. Appropriate software coding may readily be prepared by skilled programmers based on the teachings of the present disclosure, as will be apparent to those skilled in the software art.

It is to be understood that the embodiments described herein may be conveniently implemented in forms of a software package. Such a software package may be a computer program product which employs a non-transitory computer-readable storage medium including stored computer code which is used to program a computer to perform the disclosed functions and processes disclosed herein. The non-transitory computer-readable storage medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable non-transitory media for storing electronic instructions.

It is understood that the specific order or hierarchy of steps in the foregoing disclosed methods are examples of exemplary approaches. Based upon design preferences, it is understood that the specific order or hierarchy of steps in the method can be rearranged while remaining within the scope of the present invention. The accompanying method claims present elements of the various steps in a sample order, and are not meant to be limited to the specific order or hierarchy presented.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It is believed that the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed:

1. A method of using a continuous flow apparatus for performing a continuous flow nucleic acid extraction on a nucleic acid sample, comprising
    opening a first valve and a second valve attached to a piston;
    delivering a first buffer to a column, the column containing, a nucleic acid sample and a matrix, thereby causing the buffer to mix with the nucleic acid sample;
    closing the first valve and the second valve;
    directing the piston into the column causing the first buffer to be expelled from the column into a first collection tube;
    opening the first valve and the second valve; and directing the piston out of the column.

2. The method of claim 1, wherein
    the matrix is a nucleic acid matrix; and
    the first collection tube is a waste collection tube.

3. The method of claim 2 further comprising
    opening the first valve and the second valve attached to the piston;
    delivering a washing buffer to the column, causing the washing buffer to mix with a nucleic acid sample;
    closing the first valve and the second valve;
    directing the piston into the column, thereby causing the washing buffer to move from the column into the first collection tube;
    opening the first valve and the second valve; directing the piston out of the column.

4. The method of claim 3 further comprising
    opening the first valve and the second valve attached to the piston;
    delivering a second washing buffer to the column, causing the second washing buffer to mix with a nucleic acid sample;
    closing the first valve and the second valve;
    directing the piston into the column, thereby causing the second washing buffer to move from the column into the first collection tube;
    opening the first valve and the second valve; directing the piston out of the column.

5. The method of claim 4 further comprising
    moving the first collection tube away from the column and moving a second collection tube to contact the column, wherein the second collection tube is a sample collection tube;
    delivering a third buffer to the column, causing the buffer to mix with a nucleic acid sample;
    closing the first valve and the second valve;
    moving the piston into the column causing the the third buffer to move from the column into a second collection tube.

6. The method of claim 5 wherein
    the means for moving the first collection tube and the second collection tube are a rail.

7. The method of claim 1, wherein
    matrix is a cellular component matrix; and the first collection is a sample collection tube.

8. The method of claim 7 further comprising
    moving the first collection tube away from the column and moving a second collection tube to contact the column, wherein the second collection tube is a waste collection tube;

delivering a third buffer to the column, causing the buffer to mix with a nucleic acid sample;

closing the first valve and the second valve;

moving the piston into the column causing the the third buffer to move from the column into a second collection tube.

9. The method of claim 8 wherein the means for moving the first collection tube and the second collection tube are a rail.

* * * * *